United States Patent [19]
Martinez et al.

[11] Patent Number: 5,643,575
[45] Date of Patent: Jul. 1, 1997

[54] NON-ANTIGENIC BRANCHED POLYMER CONJUGATES

[75] Inventors: Anthony Martinez, Hamilton Square; Richard B. Greenwald, Somerset, both of N.J.

[73] Assignee: Enzon, Inc., Piscataway, N.J.

[21] Appl. No.: 143,403

[22] Filed: Oct. 27, 1993

[51] Int. Cl.$^6$ .................. A61K 39/385; A61K 38/54; C07K 17/08; C08G 83/00
[52] U.S. Cl. .................. 424/194.1; 424/178.1; 424/193.1; 424/195.11; 424/94.3; 530/395; 530/391.1; 530/402; 530/408; 530/409; 525/54.11
[58] Field of Search .................. 525/54.11; 530/395, 530/391.1, 402, 408, 409; 424/194.1, 195.11, 193.1, 178.1, 94.3

[56] References Cited

U.S. PATENT DOCUMENTS

| | | |
|---|---|---|
| 4,101,380 | 7/1978 | Rubinstein et al. . |
| 4,179,337 | 12/1979 | Davis et al. . |
| 4,275,000 | 6/1981 | Ross . |
| 4,680,338 | 7/1987 | Sundoro . |
| 4,766,106 | 8/1988 | Katre et al. .................. 514/12 |
| 4,846,548 | 7/1989 | Klainer .................. 350/96.29 |
| 4,889,916 | 12/1989 | Packard et al. .................. 525/54.1 |
| 4,904,582 | 2/1990 | Tullis . |
| 5,091,176 | 2/1992 | Braatz et al. . |
| 5,091,542 | 2/1992 | Ahlem et al. .................. 548/521 |
| 5,093,531 | 3/1992 | Sano et al. . |
| 5,122,614 | 6/1992 | Zalipsky . |
| 5,183,660 | 2/1993 | Ikeda et al. . |
| 5,214,131 | 5/1993 | Sano et al. . |
| 5,219,564 | 6/1993 | Zalipsky et al. .................. 424/78.17 |
| 5,229,490 | 7/1993 | Tam .................. 530/324 |
| 5,252,714 | 10/1993 | Harris et al. . |
| 5,281,698 | 1/1994 | Nitecki .................. 530/351 |
| 5,321,095 | 6/1994 | Greenwald .................. 525/404 |
| 5,324,844 | 6/1994 | Zalipsky .................. 548/520 |
| 5,514,379 | 5/1996 | Weissleder et al. .................. 424/426 |
| 5,543,158 | 8/1996 | Gref et al. .................. 424/501 |

FOREIGN PATENT DOCUMENTS

| | | |
|---|---|---|
| 0236987 | 9/1987 | European Pat. Off. . |
| 0510356 | 10/1992 | European Pat. Off. . |
| 0539167 | 4/1993 | European Pat. Off. . |
| 9102763 | 3/1991 | WIPO . |
| 9324476 | 12/1993 | WIPO . |

OTHER PUBLICATIONS

Bogdanov, A. et al. "A New Marcomolecule as a Contrast Agent for MR Angiography: Preparation, Properties, and Animal Studies" Radiology 187: 701–706 (1993) Mailed May 20, 1993.
Nishimura et al, Enzyme 26, pp. 49–53 (1981).
Kimura et al, Proceeding of the Society for Experimental Biology and Medicine, 188, pp. 364–369 (1988).
Zalipsky et al, Eur. Polym. J., vol. 19, No. 12, pp. 1177–1183, (1983).
Ouchi et al, Drug Design and Discovery, vol. 9, pp. 93–105 (1992).
Nathan et al., "Polyethylene Glycol–Lysine Copolymers:," Polymer Preprints 31: 213–214 (1990).
Knauf et al., "Relationship of Effective Molecular Size . . . ," J Biol Chem 263: 15064–70 (1988).
Wie et al (1981) Int. Arch. Allergy Appl. Immun. 64:84–99.
Savoca et al (1979) Biochim. Biophys. Acta 578:47–53.
Sehon (1991) Int. Arch. Allergy Appl. Immunol 94:11–20.
Nucci et al (1991) Advanced Drug Delivery Reviews 6:133–151.

Primary Examiner—Michael P. Woodward
Attorney, Agent, or Firm—Michael N. Mercanti

[57] ABSTRACT

Branched, substantially non-antigenic polymers are disclosed. Conjugates prepared with the polymers and biologically active molecules such as proteins and peptides demonstrate extended circulating life in vivo. Substantially fewer sites on the biologically active material are used as attachment sites. Methods of forming the polymer, conjugating the polymers with biologically active moieties and methods of using the conjugates are also disclosed.

40 Claims, No Drawings

NON-ANTIGENIC BRANCHED POLYMER CONJUGATES

BACKGROUND OF THE INVENTION

1. Field of the Invention

The present invention relates to branched polymers which are useful in extending the in vivo circulating life of biologically active materials. The invention also relates to conjugates made with the polymers.

Some of the initial concepts of coupling peptides or polypeptides to poly(ethylene glycol) PEG and similar water-soluble poly(alkylene oxides) are disclosed in U.S. Pat. No. 4,179,337, the disclosure of which is incorporated herein by reference. Polypeptides modified with these polymers exhibit reduced immunogenicity/antigenicity and circulate in the bloodstream longer than unmodified versions.

To conjugate poly(alkylene oxides), one of the hydroxyl end-groups is converted into a reactive functional group. This process is frequently referred to as "activation" and the product is called an "activated poly(alkylene oxide)". Other substantially non-antigenic polymers are similarly "activated" or functionalized.

The activated polymers are reacted with a therapeutic agent having nucleophilic functional groups that serve as attachment sites. One nucleophilic functional group commonly used as an attachment site is the $\epsilon$-amino groups of lysines. Free carboxylic acid groups, suitably activated carbonyl groups, oxidized carbohydrate moieties and mercapto groups have also been used as attachment sites.

Insulin and hemoglobin were among the first therapeutic agents conjugated. These relatively large polypeptides contain several free $\epsilon$-amino attachment sites. A sufficient number of polymers could be attached to reduce immunogenicity and increase the circulating life without significant loss of biologic activity.

Excessive polymer conjugation and/or conjugation involving a therapeutic moiety's active site where groups associated with bioactivity are found, however, often result in loss of activity and thus therapeutic usefulness. This is often the case with lower molecular weight peptides which have few attachment sites not associated with bioactivity. Many non-peptide therapeutics also lack a sufficient number of attachment sites to obtain the benefit of polymer modification.

One suggestion for overcoming the problems discussed above is to use longer, higher molecular weight polymers. These materials, however, are difficult to prepare and expensive to use. Further, they provide little improvement over more readily available polymers.

Another alternative suggested is to attach two strands of polymer via a triazine ring to amino groups of a protein. See, for example, Enzyme, 26, 49–53 (1981) and *Proc. Soc. Exper. Biol. Med.*, 188, 364–9 (1988).

Research in this area has continued. Triazine is a toxic substance which is difficult to reduce to acceptable levels after conjugation. In addition, triazine is a planar group and can only be double-polymer substituted. The planar structure rigidly locks the two polymer chains in place. This limits the benefits of polymer conjugation to about the same as that obtained by increasing polymer chain length. Thus, non-triazine-based activated polymers would offer substantial benefits to the art. The present invention addresses this need.

SUMMARY OF THE INVENTION

In one aspect of the invention, there are provided branched, substantially non-antigenic polymers corresponding to the formula:

$$(R)_n L-A \quad (I)$$

wherein (R) includes a water-soluble non-antigenic polymer;

(n)=2 or 3;

(L) is an aliphatic linking moiety covalently linked to each (R); and (A) represents an activating functional group capable of undergoing nucleophilic substitution. For example, (A) can be a group which is capable of bonding with biologically active nucleophiles or moieties capable of doing the same.

In particularly preferred aspects of the invention, (R) includes a poly(alkylene oxide) PAO such as a poly(ethylene glycol) PEG.

These umbrella-like branched polymers of the present invention (U-PAO's or U-PEG's) react with biologically active nucleophiles to form conjugates. The point of polymer attachment depends upon the functional group (A). For example, (A) can be a succinimidyl succinate or carbonate and react with epsilon amino lysines. The branched polymers can also be activated to link with any primary or secondary amino group, mercapto group, carboxylic acid group, reactive carbonyl group or the like found on biologically-active materials. Other groups are apparent to those of ordinary skill in the art.

Other aspects of the invention include conjugates containing biologically-active materials and one or more of the branched polymers described above as well as methods of their preparation. The biologically active materials include proteins, peptides, enzymes, medicinal chemicals or organic moieties whether synthesized or isolated from nature. The methods include contacting a biologically active material containing a nucleophile capable of undergoing a substitution reaction with a branched polymer described above under conditions sufficient to effect attachment while maintaining at least a portion of the biological activity.

The present invention also includes methods of treating various maladies and conditions. In this aspect, a mammal in need of treatment is administered an effective amount of a conjugate containing a biologically-active material such as a protein, enzyme or organic moiety and a branched polymer of the present invention.

One of the chief advantages of the present invention is that the branching of the polymers imparts an umbrella-like three-dimensional protective covering to the materials they are conjugated with. This contrasts with the string-like structure of conventional polymer conjugates. Moreover, the branching of the polymer chains from a common root allows dynamic, non-planar action in vivo. Thus, the branched polymers offer substantial benefits over straight-chained polymers of equivalent molecular weight.

A second advantage of the branched polymers is that they provide the benefits associated with attaching several strands of polymers to a bioeffecting material but require substantially fewer conjugation sites. The advantages of the branched polymers are particularly dramatic for therapeutic agents having few available attachment sites. All the desired properties of polymer conjugation are realized and loss of bioactivity is minimized.

DETAILED DESCRIPTION OF THE INVENTION

1. POLYMER SUBSTITUENTS AND FORMULA I DEFINED

The activated branched polymers of the present invention are preferably prepared from poly(alkylene oxides) (PAO's) that are water soluble at room temperatures. Within this group are alpha-substituted polyalkylene oxide derivatives such as methoxypoly (ethylene glycols) (mPEG) or other suitable alkyl substituted PAO derivatives such as those containing mono or bis terminal $C_1$–$C_4$ groups. Straight-chained non-antigenic polymers such as monomethyl PEG homopolymers are preferred. Alternative polyalkylene oxides such as other poly(ethylene glycol) homopolymers, other alkyl-poly(ethylene oxide) block copolymers, and copolymers of block copolymers of poly(alkylene oxides) are also useful.

The polymers of the present invention are represented by Formula (I):

$$(R)_n\text{-}L\text{-}A \qquad (I)$$

wherein:

(R) includes a water-soluble, substantially non-antigenic polymer;

(n)=2 or 3;

(L) is an aliphatic linking moiety covalently linked to each (R); and (A) represents an activating functional group capable of undergoing nucleophilic substitution.

Each (R) can be a water-soluble, substantially non-antigenic polymer chain. When the polymer chains are PEG or mPEG, it is preferred that each chain have a molecular weight of between about 200 and about 12,000 daltons and preferably between about 1,000 and about 10,000 daltons. Molecular weights of about 5,000 daltons are most preferred.

Alternative polymeric substances include materials such as dextrans, polyvinyl pyrrolidones, polyacrylamides or other similar non-immunogenic polymers. Such polymers are also capable of being functionalized or activated for inclusion in the invention. The foregoing is merely illustrative and not intended to restrict the type of non-antigenic polymers suitable for use herein.

In another embodiment of the invention, (R) is a branched polymer for secondary and tertiary branching from a bioactive material. Bifunctional and hetero-bifunctional active polymer esters can also be used. The polymers of the present invention can also be copolymerized with bifunctional materials such as poly(alkylene glycol) diamines to form interpenetrating polymer networks suitable for use in permeable contact lenses, wound dressings, drug delivery devices and the like. The stearic limitations and water solubility of such branching will be readily recognized by one of ordinary skill in the art. Preferably, however, the molecular weight of multiply branched polymers should not exceed 80,000 daltons.

As shown in Formula I, 2 or 3 polymer chains, designated (R) herein, are joined to the aliphatic linking moiety (L). Suitable aliphatics include substituted alkyl diamines and triamines, lysine esters and malonic ester derivatives. The linking moieties are preferably non-planar, so that the polymer chains are not rigidly fixed. The linking moiety (L) is also the means for attaching the multiple polymer chains or "branches" to (A), the moiety through which the polymer attaches to bio-effecting materials.

(L) preferably includes a multiply-functionalized alkyl group containing up to 18, and more preferably between 1–10 carbon atoms. A heteroatom such as nitrogen, oxygen or sulfur may be included within the alkyl chain. The alkyl chain may also be branched at a carbon or nitrogen atom. In another aspect of the invention, (L) is a single nitrogen atom.

(L) and each (R) are preferably joined by a reaction between nucleophilic functional groups on both (R) and (L). Each (R) is suitably functionalized to undergo nucleophilic substitution and bond with (L). Such functionalization of polymers is readily apparent to those of ordinary skill in the art.

A wide variety of linkages are contemplated between (R) and (L). Urethane (carbamate) linkages are preferred. The bond can be formed, for example, by reacting an amino group such as 1,3-diamino-2-propanol with methoxypolyethylene glycol succinimidyl carbonate described in U.S. Pat. No. 5,122,614, the disclosure of which is incorporated herein by reference. Amide linkages, which can be formed by reacting an amino-terminated non-antigenic polymer such as methoxy-polyethylene glycol-amine (mPEG amine) with an acyl chloride functional group.

Examples of other linkages between (R) and (L) include ether, amine, urea, and thio and thiol analogs thereof, as well as the thio and thiol analogs of the above-discussed urethane and amide linkages. The linkages are formed by methods well understood by those of ordinary skill in the art. Other suitable linkages and their formation can be determined by reference to the above-cited U.S. Pat. No. 4,179,337.

The moiety (A) of Formula I represents groups that "activate" the branched polymers of the present invention for conjugation with biologically active materials.

(A) can be a moiety selected from:

I. Functional groups capable of reacting with an amino group such as:

a) carbonates such as the p-nitrophenyl, or succinimidyl;

b) carbonyl imidazole;

c) azlactones;

d) cyclic imide thiones; or e) isocyanates or isothiocyanates.

II. Functional groups capable of reacting with carboxylic acid groups and reactive carbonyl groups such as:

a) primary amines; or b) hydrazine and hydrazide functional groups such as the acyl hydrazides, carbazates, semicarbamates, thiocarbazates, etc.

III. Functional groups capable of reacting with mercapto or sulfhydryl groups such as phenyl glyoxals; see, for example, U.S. Pat. No. 5,093,531, the disclosure of which is hereby incorporated by reference.

IV. Other nucleophiles capable of reacting with an electrophilic center. A non-limiting list includes, for example, hydroxyl, amino, carboxyl, thiol groups, active methylene and the like.

The moiety (A) can also include a spacer moiety located proximal to the aliphatic linking moiety, (L). The spacer moiety may be a heteroalkyl, alkoxy, alkyl containing up to 18 carbon atoms or even an additional polymer chain. The spacer moieties can added using standard synthesis techniques. It is to be understood that those moieties selected for (A) can also react with other moieties besides biologically active nucleophiles.

2. SYNTHESIS OF BRANCHED POLYMERS

The branched polymers (generally, U-PAO's or U-PEG's) are formed using conventional reaction techniques. For each polymer chain (R) attached, the linking compound (L) has a number of nucleophilic functional groups which correspond to (n), (i.e. 2 or 3). In one aspect, a succinimidyl carbonate active ester of the branched polymer is prepared by contacting a branched polymer subunit $(R)_nL$, prepared as described above, with p-nitrophenyl chloroformate and thereafter with N-hydroxysuccinimide to form a succinimidyl carbonate. Alternatively, the hydroxy moiety can be reacted with bis-succinimidyl carbonate directly. The polymer subunit $(R)_nL$ will include hydroxyl, amino, carboxyl and thiol groups, and the like, as well as amino or methylene hydrogens so that it can be attached to (A).

The branched polymers can also be formed by reacting aliphatic linking compounds substituted with nucleophilic functional groups such as di- or tri-amino, mercapto alcohols or alkyl triols with an activated or functionalized polymer chain such as SC-PEG, PEG-NCO, PEG-NCS, SS-PEG, PEG-acids and acid derivatives. Such methods are preferred because functionalized polymer chains and suitable aliphatic linking groups are either commercially available or readily synthesized.

Other aspects of synthesis include reacting a polymer functionalized with a nucleophilic moiety such as PEG-alcohol, PEG-amine or PEG-mercaptan with bifunctional molecules such as malonic acid derivatives or glyoxalic acid derivatives.

For example, two moles of methoxy-poly(ethylene glycol) amine can be reacted with a substituted or unsubstituted malonyl chloride to form a compound of Formula (II):

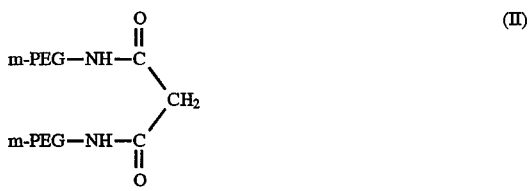

Reaction with strong base converts the methylene linker into an anion that can be further functionalized.

Likewise, two moles of methoxy-poly(ethylene glycol) succinimidyl carbonate may be reacted with a 1,3 diamino 2-propanol to form a compound of Formula (III):

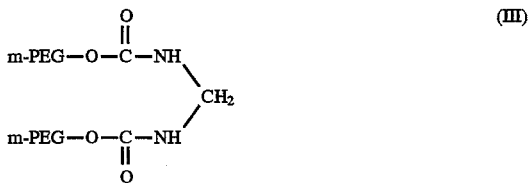

Similarly, two moles of mPEG can be reacted with a triamine such as diethylenetriamine to form a compound having the structure of Formula (IV):

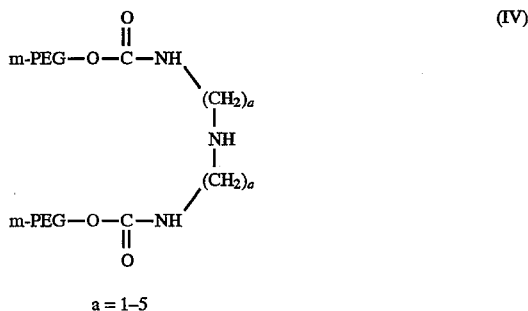

a = 1–5

Branched polymer (III) can then be activated by first functionalizing with compounds capable of activating the hydroxyl group such as p-nitrophenyl chloroformate to form a reactive p-nitrophenyl carbonate. The resulting p-nitrophenyl carbonate polymer can be directly reacted with a biologically active nucleophile.

The p-nitrophenyl carbonate polymer can also serve as an intermediate. It can be reacted with a large excess of N-hydroxysuccinimide to form a succinimidyl carbonate-activated branched polymer. Other routes to succinimidyl carbonates are available and contemplated for use herein. Alternatively, a p-nitrophenyl carbonate polymer intermediate can be reacted with anhydrous hydrazine to form a carbazate branched polymer.

Branched polymer (IV) can be activated by reacting (IV) with a hydroxy acid such as lactic acid to form the hydroxy amide. Thereafter, the hydroxy amide is functionalized in the same manner discussed above for (III).

As will be readily appreciated, numerous variations and combinations of the reaction between the functionalized polymer chains and aliphatic linking compound can be utilized to form the compounds of the present invention. The foregoing reactions were disclosed to illustrate the present invention.

Branched polymers corresponding to Formula (II), Formula (III), and the like, can also be extended with a spacer moiety, designated herein as $R_2$, between the aliphatic linking moiety and the group capable of undergoing nucleophilic substitution. For example, the polymer of Formula (III) with a spacer moiety is represented by Formula (V):

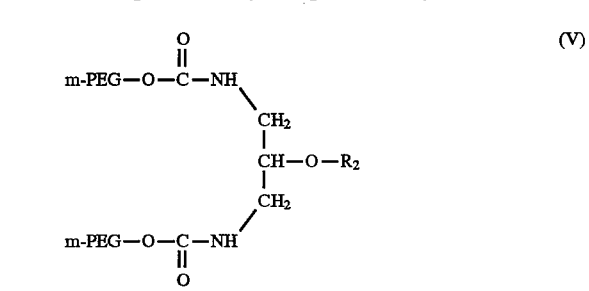

Spacer moieties represented by ($R_2$) include but are not limited to:

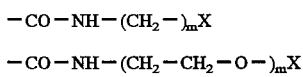

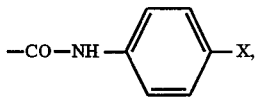

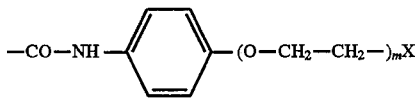

and the like, where (m) is an integer between 1 and 18 inclusive and (X)=H, OH, $NH_2$, COOH. Depending upon the circumstances, an —H of an —OH group is attached to the end of the spacer moiety to form the terminal hydroxyl group.

Synthesis of compounds corresponding to (V) include reacting the p-nitrophenyl carbonate or N-succinimidyl carbonate active esters of Formula (III) compounds with reagents such as

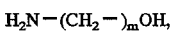

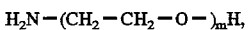

aminophenols, or

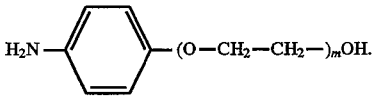

The attachment of spacer moieties to a branched polymer is described with reference to the polymer of Formula (II)

for purposes of illustration, not limitation. Similar products would be obtained with any of the branched polymers disclosed by the present invention. For example, spacer moieties ($R_2$) can be joined to linker moieties (L) substituted with groups other than hydroxyl groups. When the hydroxyl group is replaced by an amino group, or when the carbon substituted with hydroxyl groups is replaced by a secondary amine, (L) can be reacted with suitable reagents such as substituted isocyanates or isothiocyanates and the like. Like the aliphatic linking moieties described above, the terminal groups of the spacer moieties can be similarly functionalized to react with nucleophiles.

After synthesis, the activated branched polymers can be purified by conventional methods and reacted with biologically active materials containing nucleophiles capable of bonding with the polymer while maintaining at least some of the activity associated with the material in unmodified form.

3. BIOLOGICALLY ACTIVE MATERIALS SUITABLE FOR CONJUGATION

The nucleophiles conjugated with the branched polymers are described as "biologically active". The term, however, is not limited to physiological or pharmacological activities. For example, some nucleophile conjugates such as those containing enzymes, are able to catalyze reactions in organic solvents. Likewise, some inventive polymer conjugates containing proteins such as concanavalin A, immunoglobulin and the like are also useful as laboratory diagnostics. A key feature of all of the conjugates is that at least some portion of the activity associated with the unmodified bio-active material is maintained.

The conjugates are biologically active and have numerous therapeutic applications. Mammals in need of treatment which includes a biologically active material can be treated by administering an effective amount of a polymer conjugate containing the desired bioactive material. For example, mammals in need of enzyme replacement therapy or blood factors can be given branched polymer conjugates containing the desired material.

Biologically active nucleophiles of interest of the present invention include, but are not limited to, proteins, peptides, polypeptides, enzymes, organic molecules of natural and synthetic origin such as medicinal chemicals and the like.

Enzymes of interest include carbohydrate-specific enzymes, proteolytic enzymes, oxidoreductases, transferases, hydrolases, lyases, isomerases and ligases. Without being limited to particular enzymes, examples of enzymes of interest include asparaginase, arginase, arginine deaminase, adenosine deaminase, superoxide dismutase, endotoxinases, catalases, chymotrypsin, lipases, uricases, adenosine diphosphatase, tyrosinases and bilirubin oxidase. Carbohydrate-specific enzymes of interest include glucose oxidases, glucodases, galactosidases, glucocerebrosidases, glucouronidases, etc.

Proteins, polypeptides and peptides of interest include, but are not limited to, hemoglobin, serum proteins such as blood factors including Factors VII, VIII, and IX; immunoglobulins, cytokines such as interleukins, α-, β- and γ-interferons, colony stimulating factors including granulocyte colony stimulating factors, platelet derived growth factors and phospholipase-activating protein (PLAP). Other proteins of general biological or therapeutic interest include insulin, plant proteins such as lectins and ricins, tumor necrosis factors and related alleles, growth factors such as tissue growth factors, such as TGFα's or TGFβ's and epidermal growth factors, hormones, somatomedins, erythropoietin, pigmentary hormones, hypothalamic releasing factors, antidiuretic hormones, prolactin, chorionic gonadotropin, follicle-stimulating hormone, thyroid-stimulating hormone, tissue plasminogen activator, and the like. Immunoglobulins of interest include IgG, IgE, IgM, IgA, IgD and fragments thereof.

Some proteins such as the interleukins, interferons and colony stimulating factors also exist in non-glycosylated form, usually as a result of using recombinant techniques. The non-glycosylated versions are also among the biologically active nucleophiles of the present invention.

The biologically active nucleophiles of the present invention also include any portion of a polypeptide demonstrating in vivo bioactivity. This includes amino acid sequences, antisense moieties and the like, antibody fragments, single chain binding antigens, see, for example U.S. Pat. No. 4,946,778, disclosure of which is incorporated herein by reference, binding molecules including fusions of antibodies or fragments, polyclonal antibodies, monoclonal antibodies, catalytic antibodies, nucleotides and oligonucleotides.

The proteins or portions thereof can be prepared or isolated by using techniques known to those of ordinary skill in the art such as tissue culture, extraction from animal sources, or by recombinant DNA methodologies. Transgenic sources of the proteins, polypeptides, amino acid sequences and the like are also contemplated. Such materials are obtained form transgenic animals, i.e., mice, pigs, cows, etc., wherein the proteins expressed in milk, blood or tissues. Transgenic insects and baculovirus expression systems are also contemplated as sources. Moreover, mutant versions of proteins, such as mutant TNF's and/or mutant interferons are also within the scope of the invention.

Other proteins of interest are allergen proteins such as ragweed, Antigen E, honeybee venom, mite allergen, and the like.

Useful biologically active nucleophiles are not limited to proteins and peptides. Essentially any biologically-active compound is included within the scope of the present invention. The present invention is particularly well-suited for compounds which have few or even a single nucleophilic attachment site for polymer conjugation such as medicinal chemicals whether isolated from nature or synthesized. Chemotherapeutic molecules such as pharmaceutical chemicals i.e. anti-tumor agents including taxol, taxanes, taxoid molecules, anthracyclines and methotrexates, cardiovascular agents, anti-neoplastics, anti-infectives, anti-anxiety agents, gastrointestinal agents, central nervous system-activating agents, analgesics, fertility or contraceptive agents, anti-inflammatory agents, steroidal agents, anti-urecemic agents, cardiovascular agents, vasodilating agents, vasoconstricting agents and the like.

The foregoing is illustrative of the biologically active nucleophiles which are suitable for conjugation with the polymers of the invention. It is to be understood that those biologically active materials not specifically mentioned but having suitable nucleophilic groups are also intended and are within the scope of the present invention.

4. SYNTHESIS OF BIOLOGICALLY ACTIVE CONJUGATES

One or more of the activated branched polymers can be attached to a biologically active nucleophile by standard chemical reactions. The conjugate is represented by the formula: (VI)

[(R)$_n$-L-A$^1$]$_z$-(nucleophile)

wherein (R) is a water-soluble substantially non-antigenic polymer; n=2 or 3; (L) is an aliphatic linking moiety; (A$^1$) represents a linkage between (L) and the nucleophile and (z) is an integer ≧1 representing the number of polymers conjugated to the biologically active nucleophile. The upper limit for (z) will be determined by the number of available nucleophilic attachment sites and the degree of polymer attachment sought by the artisan. The degree of conjugation can be modified by varying the reaction stoichiometry using well-known techniques. More than one polymer conjugated to the nucleophile can be obtained by reacting a stoichiometric excess of the activated polymer with the nucleophile.

The biologically active nucleophiles can be reacted with the activated branched polymers in an aqueous reaction medium which can be buffered, depending upon the pH requirements of the nucleophile. The optimum pH for the reaction is generally between about 6.5 and about 8.0 and preferably about 7.4 for proteinaceous/polypeptide materials. Organic/chemotherapeutic moieties can be reacted in non-aqueous systems. The optimum reaction conditions for the nucleophile's stability, reaction efficiency, etc. is within level of ordinary skill in the art. The preferred temperature range is between 4° C. and 37° C. The temperature of the reaction medium cannot exceed the temperature at which the nucleophile may denature or decompose. It is preferred that the nucleophile be reacted with an excess of the activated branched polymer. Following the reaction, the conjugate is recovered and purified such as by diafiltration, column chromatography, combinations thereof, or the like.

It can be readily appreciated that the activated branched non-antigenic polymers of the present invention are a new and useful tool in the conjugation of biologically active materials, especially when they lack a sufficient number of suitable polymer attachment sites.

EXAMPLES

The following non-limiting examples illustrate certain aspects of the invention. All parts and percentages are by weight unless otherwise noted and all temperatures are in degrees Celsius.

MATERIALS

Methoxypoly(ethylene glycol) (m-PEG) was obtained from Union Carbide. The solvents were obtained from Aldrich Chemical of Milwaukee, Wis. The methoxy-poly (ethylene glycol)-N-succinimidyl carbonate (SC-PEG) was prepared as described in U.S. Pat. No. 5,122,614, using m-PEG having a molecular weight of about 5,000. Each of the products prepared in Examples 1–9 were confirmed structurally by carbon—13 NMR.

EXAMPLE 1—U-PEG-OH

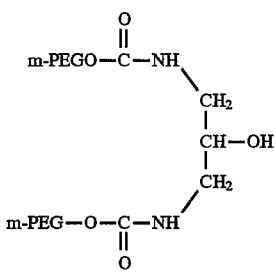

This branched polymer was prepared by adding 100 mg (1.1 mmol) of 1,3-diamino-2-propanol to a solution of 10.0 g (2 mmol) of SC-PEG in 50 mL of methylene chloride. The mixture was stirred for 18 hours at room temperature then filtered. Excess solvent was removed by distillation in vacuo. The residue was recrystallized from 2-propanol to yield 7.1 g of product (70% yield).

EXAMPLE 2—U-PNP-PEG

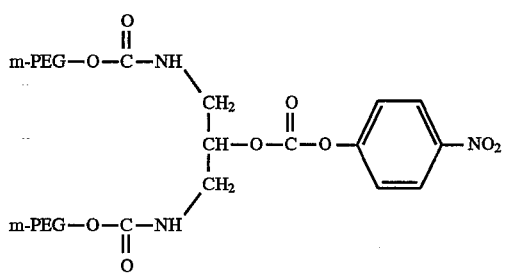

The compound of Example 1 was activated with p-nitrophenyl chloroformate. First, 5.0 g (0.5 mmol) of U-PEG was azeotropically dried by refluxing in 75 mL of toluene for 2 hours, resulting in the removal of 25 mL of solvent/water. The reaction mixture was cooled to 30° C., followed by the addition of 120 mg (0.6 mmol) of p-nitrophenyl chloroformate and 50 mg (0.6 mmol) of pyridine. The resulting mixture was stirred for two hours at 45° C., followed by stirring overnight at room temperature.

The reaction mixture was then filtered through CELITE™, followed by removal of the solvent from the filtrate by distillation in vacuo. The residue was recrystallized from 2-propanol to yield 4.2 g (81% yield) of the product.

EXAMPLE 3—US-PEG

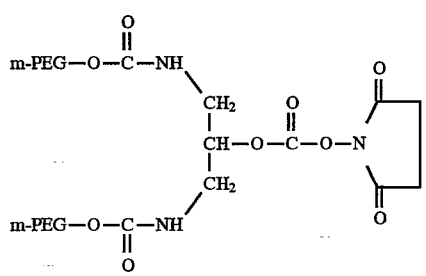

In this example, the U-PNP PEG of Example 2 was reacted with N-hydroxysuccinimide to form the succinimidyl carbonate ester of U-PEG. A solution containing 5.0 g (0.5 mmol) of the U-PNP PEG, 0.6 g (5 mmol) of N-hydroxysuccinimide and 0.13 g (1 mmol) of diisopropylethylamine in 40 ml of methylene chloride was refluxed for 18 hours. The solvent was then removed by distillation in vacuo, and the residue was recrystallized from 2-propanol to yield 4.2 g of the succinimidyl carbonate ester (82% yield).

EXAMPLE 4—NU-PNP-PEG

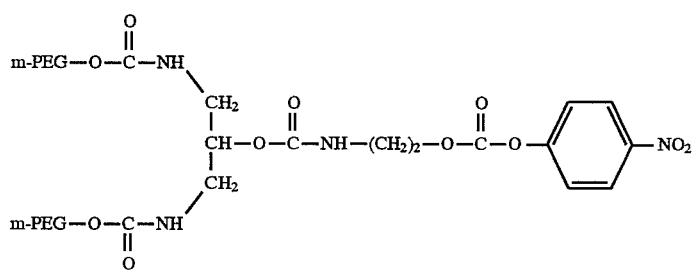

This branched polymer above was prepared by reacting U-PNP PEG (Ex. 2) with ethanolamine followed by p-nitrophenyl chloroformate.

A solution containing 5.0 g (0.5 mmol) of U-PNP PEG in 40 mL of methylene chloride was combined with 60 mg (1 mmol) of ethanolamine and stirred overnight at room temperature. Thereafter, the solvent was removed by distillation in vacuo. The residue was recrystallized from 2-propanol to yield 4.3 g of the intermediate (84% yield) shown below:

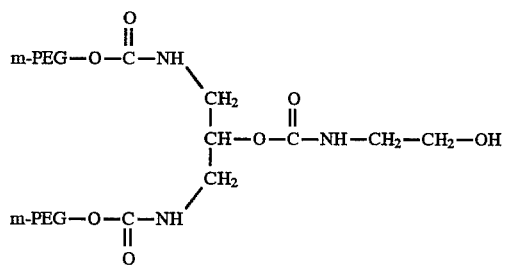

The NU-PEG-OH was prepared by reacting the above intermediate with p-nitrophenyl chloroformate. The intermediate was azeotropically dried by refluxing, 2.0 g (0.2 mmol) in 40 mL toluene for two hours, with the removal of 25 mL of solvent/water. The reaction mixture was cooled, followed by the addition of 0.3 mmol p-nitrophenyl chloroformate and 0.3 mmol pyridine, according to the procedure of Example 2. The resulting mixture was stirred for two hours at 45° C., followed by stirring overnight at room temperature.

The NU-PEG-OH was also recovered by the procedure in Example 2 to yield 1.5 g (71% yield).

EXAMPLE 5—XU-PEG-OH

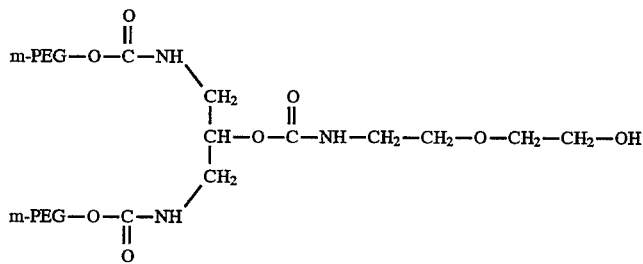

This branched polymer was prepared by reacting the U-PNP PEG of Example 2 with 2-(2-aminoethoxy) ethanol according to the procedure described in Example 4, (i.e., the amino alcohol was reacted with the p-nitrophenyl carbonate). The recrystallized product yield was 86%.

EXAMPLE 6—XU-PNP-PEG

The compound of Example 5 was functionalized with p-nitrophenyl carbonate as in Examples 2 and 4. The recrystallized product yield was 83%.

EXAMPLE 7—XUS-PEG

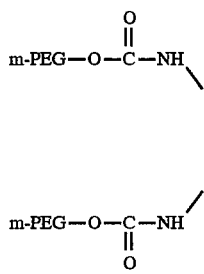 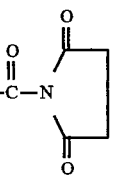

In this example, the succinimidyl carbonate derivative of compound prepared in Example 5 was prepared according to the process described in Example 3, by reacting N-hydroxysuccinimide with the p-nitrophenyl carbonate derivative of Example 6. The recovered product yield was 84%.

EXAMPLE 8—U-LYS-PEG

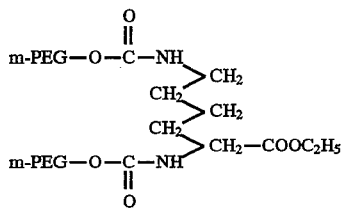

The branched polymer depicted above was prepared by reacting U-PNP PEG with lysine ethyl ester. In particular, a mixture of 5.0 g (1.0 mmol) of the polymer, 150 mg (0.6 mmol) of lysine dihydrochloride and 140 mg (1.8 mmol) of pyridine was refluxed for 18 hours. The solvent was removed by distillation in vacuo. The residue was recrystallized from 2-propanol to yield 4.5 g (88% yield) of product.

EXAMPLE 9—Synthesis of m-PNP-PEG

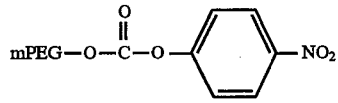

A solution of 50 g (0.01 moles) of m-PEG-OH (MW= 5000) in 500 ml of toluene was azeotroped for 2 hrs, while removing 100 ml of toluene/water. The reaction mixture was cooled to 30° C., followed by addition of 2.6 g (0.013 moles) of p-nitrophenyl chloroformate and 1.0 ml (0.013 moles) of pyridine. The resulting mixture was stirred for two hours at 45° C., followed by stirring overnight at room temperature.

The reaction mixture was then filtered through CELITE™, followed by removal of the solvent by distillation in vacuo. The residue was recrystallized from 2-propanol to yield 48.2 g (93% yield) of the product.

EXAMPLES 10 and 11

Conjugates of erythropoietin (EPO) with US-PEG (Example 3) were prepared by dialyzing two 3.0 mg EPO samples (human recombinant Chinese Hamster Ovary (CHO) cell culture) into 0.1 M phosphate buffer pH 7.0 solutions using a Centricon-10 (Amicon Corporation, Beverly, Mass.). The first EPO solution was combined with 1.954 mg (2-fold molar excess) of the US-PEG while the second EPO solution was combined with 3.908 mg (4-fold molar excess) of the US-PEG. The reaction mixtures were stirred for one hour at room temperature (about 22°–25° C.). The excess polymer was removed by centrifugation and the reaction mixtures were dialyzed into 10 mM phosphate buffer, pH 8.0. Unreacted EPO was removed on an ion-exchange column (2-HD column, Sepracor).

SDS-PAGE analysis confirmed that for both reaction mixtures, about two to three of the branched polymers were covalently bound to each protein molecule. The EPO activity of the conjugates was measured by colorometric assay with DA 1-K cells, a murine lymphoblastic cell line dependent on IL-3, GM-CSF and EPO for growth. The cells are grown in IMDM containing 5% FCS and incubated at 37° C. in 5% $CO_2$ in air. The assay time is 72 hours and cell growth is monitored by MTT dye uptake. In the assay, both conjugate samples retained 40–50% of the activity of the unconjugated EPO.

EXAMPLES 12 and 13

Tumor Necrosis Factor (TNF) was conjugated with the XUS-PEG of Example 7. As a comparison, the TNF was also conjugated with the linear SC PEG, methoxypoly (ethylene glycol) succinimidyl carbonate of U.S. Pat. No. 5,122,614. Both conjugates were prepared by reacting a 500 micrograms of TNF, 2.0 mg/mL, with a 25-fold molar excess of the polymer. Each reaction was carried out for 140 minutes on ice.

The $ED_{50}$ for the branched conjugate was 0.29 ng/mL for the concentration-response curve generated by dilutions of 0.1 micrograms/mL and 0.625 ng/mL for the concentration-response curve generated by dilutions of 0.01 micrograms/mL. The $ED_{50}$ for unmodified TNF of 0.01–0.02 ng/mL. The $ED_{50}$ for the linear succinimidyl carbonate conjugates, ranged between 8 and 19 ng/mL.

In vitro tumoricidal and toxicity data indicated that the branched conjugate appears to be more cytotoxic than the non-branched conjugate.

While there have been described what are presently believed to be the preferred embodiments of the invention, those skilled in the art will realize that changes and modifications may be made without departing from the sprit of the invention. It is intended to cliam all such changes and modification s as fall within the true scope of the invention.

What is claimed is:

1. A branched substantially non-antigenic polymer comprising the formula:

wherein (R) is a water soluble, substantially non-antigenic polymer containing a $C_1$–$C_4$ terminal group;

(n)=2 or 3;

(A) is a functional group capable of bonding with a biologically active nucleophile selected from the group consisting of proteins, peptides, polypeptides, enzymes and chemotherapeutic molecules or a moiety capable of being functionalized to react with said nucleophile; and (L) is selected from the group consisting of

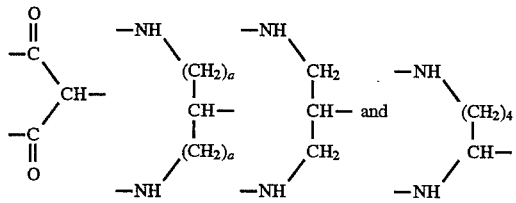

wherein (α) is 1 to 5.

2. The polymer of claim 1, wherein at least one (R) is a straight-chained polymer.

3. The polymer of claim 1, wherein at least one (R) is a poly(alkylene oxide).

4. The polymer of claim 3, wherein said poly(alkylene oxide) is an α-substituted poly(alkylene oxide).

5. The polymer of claim 3, wherein said poly(alkylene oxide) is selected from the group consisting of poly(ethylene glycol) homopolymers, alkyl-capped poly(ethylene oxides), and copolymers of block copolymers of poly(alkylene oxides).

6. The polymer of claim 5, wherein said poly(alkylene oxide) has a molecular weight between about 200 and about 20,000.

7. The polymer of claim 6, wherein said poly(alkylene oxide) has a molecular weight between 2,000 and about 10,000.

8. The polymer of claim 7, wherein said poly(ethylene glycol) homopolymer has a molecular weight of about 5,000.

9. The polymer of claim 2, wherein each (R) is a poly(ethylene glycol) homopolymer.

10. The polymer of claim 1, wherein at least one (R) is a branched polymer.

11. The activated branched polymer of claim 1, wherein (n) is two.

12. The polymer of claim 1, wherein (A) is a moiety selected from the group consisting of hydroxyl, amino, carboxyl, carbonyl, thiol and methylene hydrogen moieties.

13. The polymer of claim 1, wherein (A) is a succinimidyl or a p-nitrophenyl carbonate active ester.

14. The polymer of claim 1, wherein (A) further comprises a spacer moiety.

15. The polymer of claim 14, wherein said spacer moiety is selected from the group consisting of alkyls containing up to 18 carbon atoms, cycloalkyl groups containing up to 18 carbon atoms and polymers.

16. The polymer of claim 1, wherein at least one (R) further comprises a functional group capable of covalently bonding with nucleophiles.

17. A method of forming a biologically active conjugate, comprising: contacting a biologically active nucleophile selected from the group consisting of proteins, peptides, polypeptides, enzymes and chemotherapeutic molecules with an activated branched non-antigenic polymer having a structure represented by:

$(R)_n\text{-L-A}$ wherein:

(R) is a water-soluble substantially non-antigenic polymer containing a $C_1$–$C_4$ terminal group;

(n)=2 or 3;

(L) is selected from the group consisting of:

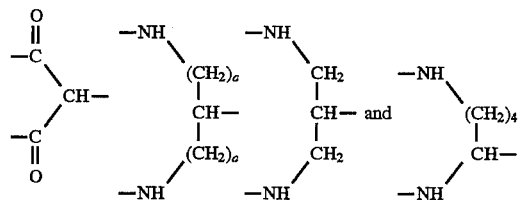

wherein (α) is 1 to 5; and (A) is a functional group capable of forming a covalent bond with said biologically active nucleophile.

18. A polymer conjugate comprising the formula:

$[(R)_n\text{-L-A}^1]_z\text{-(nucleophile)}$ wherein:

(R) is a water-soluble substantially non-antigenic polymer containing a $C_1$–$C_4$ terminal group;

(n)=2 or 3;

(L) is selected from the group consisting of:

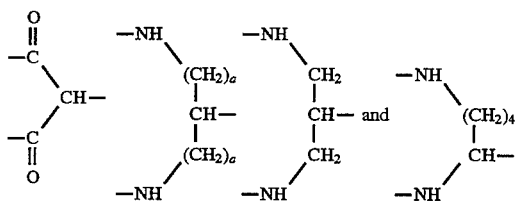

wherein (α) is 1 to 5;

(nucleophile) is a biologically active nucleophile selected from the group consisting of proteins, peptides, polypeptides, enzymes and chemotherapeutic molecules;

($A^1$) represents a covalent linkage between (L) and the biologically active nucleophile; and (z) represents the number of polymers attached to the nucleophile.

19. The conjugate of claim 18, wherein at least one (R) is a poly(alkylene oxide).

20. The conjugate of claim 19, wherein said poly(alkylene oxide is an α-substituted poly(alkylene oxide).

21. The conjugate of claim 19, wherein said poly(alkylene oxide) is selected from the group consisting of poly(ethylene glycol) homopolymers, alkyl-capped poly(ethylene oxides), and copolymers of block copolymers of poly(alkylene oxides).

22. The conjugate of claim 21, wherein said poly(alkylene oxide) has a molecular weight between about 200 and about 20,000.

23. The conjugate of claim 22, wherein said poly(alkylene oxide) has a molecular weight between 2,000 and about 10,000.

24. The conjugate of claim 23, wherein said poly(ethylene glycol) homopolymer has a molecular weight of about 5,000.

25. The conjugate of claim 19, wherein each (R) is a poly(ethylene glycol) homopolymer.

26. The conjugate of claim 18, wherein at least one (R) is a branched polymer.

27. The conjugate of claim 18, wherein (L) is a non-planar moiety.

28. The conjugate of claim 18, wherein said protein is selected from the group consisting of antibodies, monoclonal antibodies, fragments of antibodies and single chain-binding antigens.

29. The conjugate of claim 18, wherein said nucleophile is a member of the group consisting of anti-neoplastics, anti-infectives, anti-anxiety agents, anti-gastrointestinal agents, central nervous system-activating agents, analgesics, fertility, contraceptive agents, anti-inflammatory agents, steroidal agents, anti-urecemic agents, cardiovascular agents, vasodilating agents and vasoconstricting agents.

30. The conjugate of claim 29, wherein said antineoplastic agent is selected from the group consisting of taxol, taxanes, taxoid molecules, anthracyclines and methotrexates.

31. A method of treatment comprising administering to a mammal in need such treatment a therapeutically effective amount of the branched polymer conjugate of claim 20.

32. A method of preparing a succinimidyl carbonate active ester of a branched non-antigenic polymer comprising the steps of:

i) contacting a branched non-antigenic polymer having a structure represented by:

(R)$_n$-L-A wherein (R) independently comprises a water-soluble substantially non-antigenic polymer containing a $C_1$-$C_4$ terminal group;
(n)=2 or 3;
(L) is selected from the group consisting of:

$$\begin{array}{c}O\\\|\\-C\\\phantom{x}\diagdown\\\phantom{xxx}CH-\\\phantom{x}\diagup\\-C\\\|\\O\end{array}\begin{array}{c}-NH\diagdown\\\phantom{xx}(CH_2)_a\\\phantom{xx}|\\\phantom{xx}CH-\\\phantom{xx}|\\\phantom{xx}(CH_2)_a\\\phantom{x}\diagup\\-NH\end{array}\begin{array}{c}-NH\diagdown\\\phantom{xx}CH_2\\\phantom{xx}|\\\phantom{xx}CH-\\\phantom{xx}|\\\phantom{xx}CH_2\\\phantom{x}\diagup\\-NH\end{array}\text{and}\begin{array}{c}-NH\diagdown\\\phantom{xx}(CH_2)_4\\\phantom{xx}|\\\phantom{xx}CH-\\\phantom{x}\diagup\\-NH\end{array}$$

wherein (α) is 1 to 5; and
(A) is a functional group capable of forming a covalent bond with a nucleophile; with p-nitrophenyl chloroformate; and ii) reacting the p-nitrophenyl carbonate active ester of step i) with N-hydroxysuccinimide.

33. The method of claim 32, wherein (A) further comprises a spacer moiety.

34. A method of preparing a succinimidyl carbonate active ester of a branched non-antigenic polymer comprising contacting a branched non-antigenic polymer having a structure represented by:

(R)$_n$-L-A wherein (R) independently comprises a water-soluble substantially non-antigenic polymer containing a $C_1$-$C_4$ terminal group;
(n)=2 or 3;
(L) is selected from the group consisting of:

$$\begin{array}{c}O\\\|\\-C\\\phantom{x}\diagdown\\\phantom{xxx}CH-\\\phantom{x}\diagup\\-C\\\|\\O\end{array}\begin{array}{c}-NH\diagdown\\\phantom{xx}(CH_2)_a\\\phantom{xx}|\\\phantom{xx}CH-\\\phantom{xx}|\\\phantom{xx}(CH_2)_a\\\phantom{x}\diagup\\-NH\end{array}\begin{array}{c}-NH\diagdown\\\phantom{xx}CH_2\\\phantom{xx}|\\\phantom{xx}CH-\\\phantom{xx}|\\\phantom{xx}CH_2\\\phantom{x}\diagup\\-NH\end{array}\text{and}\begin{array}{c}-NH\diagdown\\\phantom{xx}(CH_2)_4\\\phantom{xx}|\\\phantom{xx}CH-\\\phantom{x}\diagup\\-NH\end{array}$$

wherein (α) is 1 to 5; and
(A) is a functional group capable of forming a covalent bond with a nucleophile with bis-succinimidyl carbonate.

35. The method of claim 34, wherein (A) further comprises a spacer moiety.

36. The polymer of claim 1, wherein said $C_1$-$C_4$ terminal group is methoxy.

37. The polymer of claim 1 wherein (A) is selected from the group consisting of carbonyl imidazole, azlactones, cyclic imide thiones, isocyanates, isothiocyanates, primary amines, hydrazines, acyl hydrazines, carbazates, semicarbazates, thiocarbazates and phenylglyoxals.

38. The polymer of claim 1 comprising a structure selected from the group consisting of:

$$\begin{array}{c}\text{m-PEG}-NH-\overset{\displaystyle O}{\underset{\|}{C}}\diagdown\\\phantom{xxxxxxxxxxxxx}CH_2,\\\text{m-PEG}-NH-\underset{\|}{\overset{\displaystyle }{C}}\diagup\\\phantom{xxxxxxxxxxx}O\end{array}$$

$$\begin{array}{c}\text{m-PEG}-O-\overset{\displaystyle O}{\underset{\|}{C}}-NH\diagdown\\\phantom{xxxxxxxxxxxxxxxx}CH_2\\\phantom{xxxxxxxxxxxxxxxx}|\\\phantom{xxxxxxxxxxxxxxxx}CH-OH,\\\phantom{xxxxxxxxxxxxxxxx}|\\\phantom{xxxxxxxxxxxxxxxx}CH_2\\\text{m-PEG}-O-\underset{\|}{\overset{\displaystyle }{C}}-NH\diagup\\\phantom{xxxxxxxxxxx}O\end{array}$$

$$\begin{array}{c}\text{m-PEG}-O-\overset{\displaystyle O}{\underset{\|}{C}}-NH\diagdown\\\phantom{xxxxxxxxxxxxxxxx}(CH_2)_a\\\phantom{xxxxxxxxxxxxxxxx}|\\\phantom{xxxxxxxxxxxxxxxx}NH\\\phantom{xxxxxxxxxxxxxxxx}|\\\phantom{xxxxxxxxxxxxxxxx}(CH_2)_a\\\text{m-PEG}-O-\underset{\|}{\overset{\displaystyle }{C}}-NH\diagup\\\phantom{xxxxxxxxxxx}O\end{array}$$

a = 1-5 and

-continued
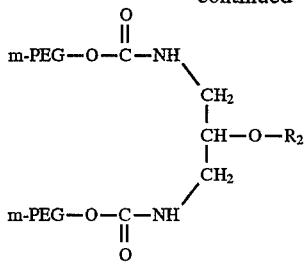
wherein a is 1 to 5 and $R_2$ is a spacer moiety selected from the group consisting of:
—CO—NH—$(CH_2—)_m$X
—CO—NH—$(CH_2—CH_2—O—)_m$X
-continued
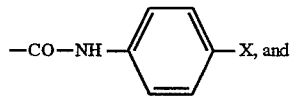
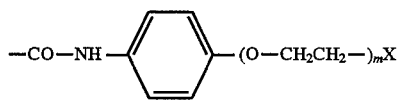
where (m) is an integer between 1 and 18 inclusive and (X) is H, OH, $NH_2$, or COOH.
39. The polymer of claim 1 comprising a structure selected from the group consisting of:
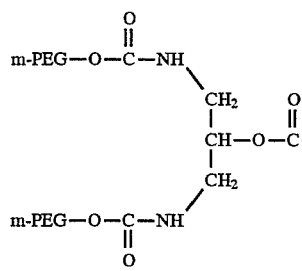 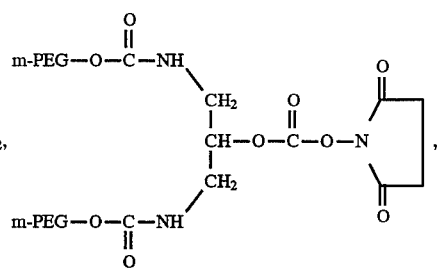
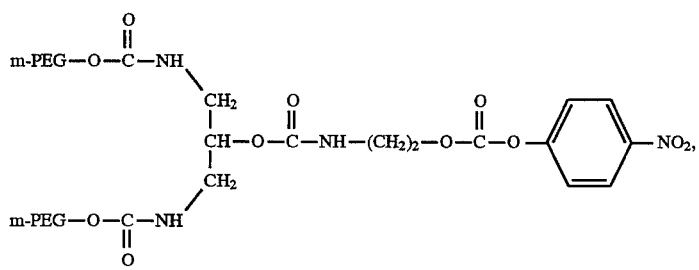
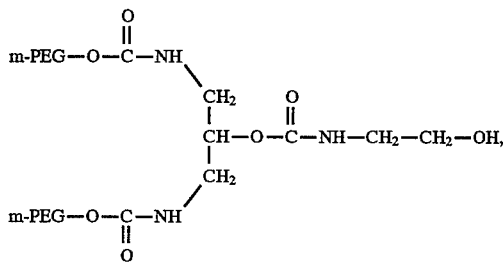
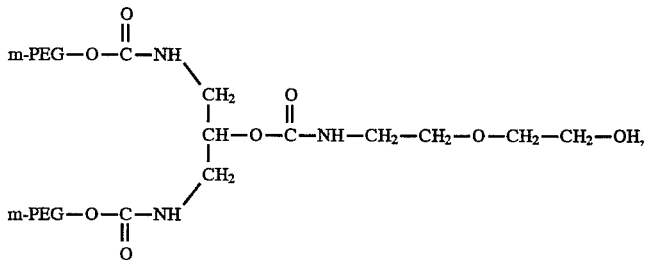

-continued
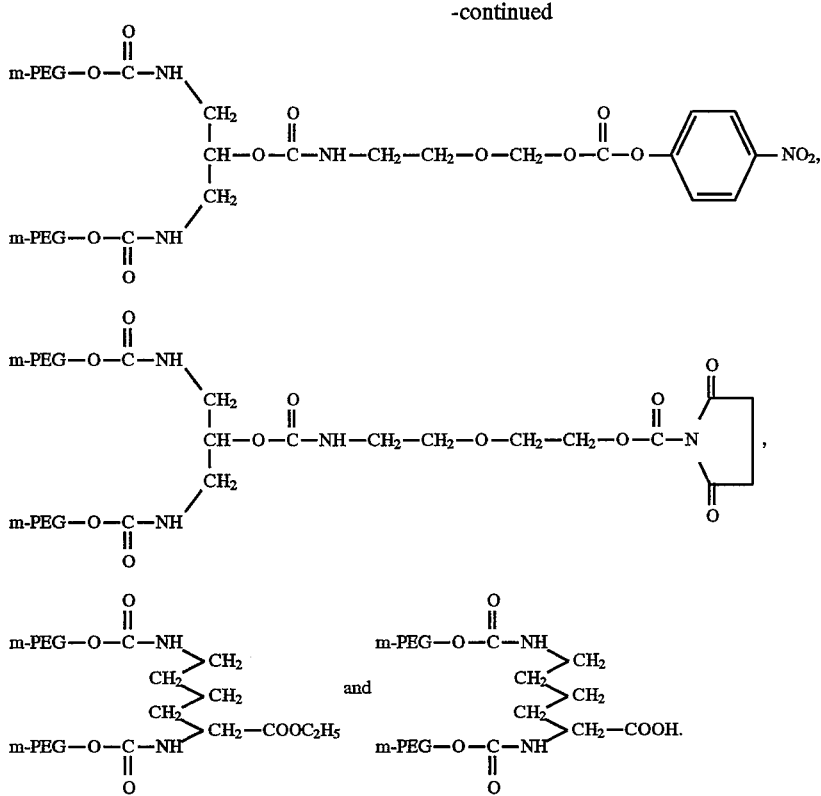
40. The polymer of claim 1, wherein said (R) is linked to said (L) by a linkage selected from the group consisting of urethane, amide, ether, amine urea, thio and thiol.
* * * * *

UNITED STATES PATENT AND TRADEMARK OFFICE
CERTIFICATE OF CORRECTION

PATENT NO. : 5,643,575
DATED : July 1, 1997
INVENTOR(S) : MARTINEZ et al.

Page 1 of 3

It is certified that error appears in the above-identified patent and that said Letters Patent is hereby corrected as shown below:

Column 3, lines 48 and 59: "multiply" should read -- multiple--,
Column 4, line 10: delete ", which"

Column 5, lines 35-41: 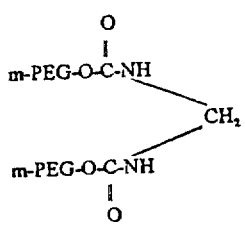 should read -- 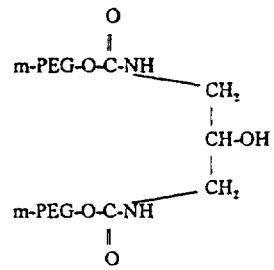 --,

Column 8, line 19: "antigens" should read --proteins--,
Column 8, line 54: delete "cardiovascular agents,", Column 13, lines 22-30: 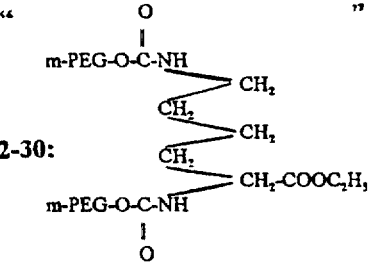 should read -- 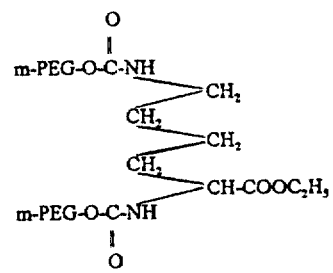 --, Column 13, line 33: "U-PNP PEG" should read --PNP-PEG--,
Column 14, line 57: "sprit" should read --spirit--,
Column 14, line 58: "cliam" should read --claim--,
Column 14, line 59: "modification s" should read --modifications--,
Claim 1, last line of the claim: "α" should read --a--,
Claim 8, line 1: "claim 7" should read --claim 5--,
Claim 17, at column 16, line 16: "α" should read --a--,
Claim 18, at column 16, line 39: "α" should read --a--,

UNITED STATES PATENT AND TRADEMARK OFFICE
CERTIFICATE OF CORRECTION

PATENT NO. : 5,643,575

DATED : July 1, 1997

INVENTOR(S) : MARTINEZ et al.

It is certified that error appears in the above-identified patent and that said Letters Patent is hereby corrected as shown below:

Claim 20, lines 1-2: "poly(alkylene oxide" should read -- poly(alkylene oxide)--, Claim 24, line 1: "claim 23" should read --claim 21--.

Claim 28, line 4: "antigens" should read --proteins--,

Claim 29, line 3: "anti-gastrointestinal" should read --gastrointestinal-- and at line 5: after "fertility" add --agents--.

Claim 31, line 3: "claim 20" should read "claim 18",

Claim 32, column 17, line 44: "α" should read --$\underline{a}$--,

Claim 34, column 18, line 12: "α" should read --$\underline{a}$--,

Claim 38, column 18, line 59: delete "a=1-5",

Claim 39, at column 21,   " " should read 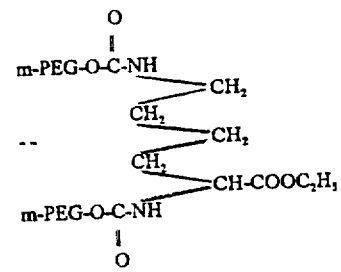

Claim 39, at columns 21 and 22,   " " should read 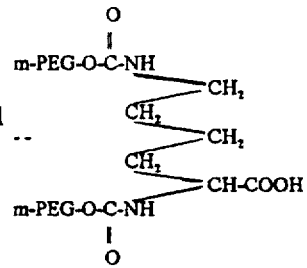

UNITED STATES PATENT AND TRADEMARK OFFICE
CERTIFICATE OF CORRECTION

PATENT NO. : 5,643,575
DATED : July 1, 1997
INVENTOR(S) : MARTINEZ et al.

It is certified that error appears in the above-identified patent and that said Letters Patent is hereby corrected as shown below:

Claim 40, last line: "amine urea" should read —amine, urea—.

Signed and Sealed this

Twelfth Day of May, 1998

Attest:

BRUCE LEHMAN

*Attesting Officer*  *Commissioner of Patents and Trademarks*